US008551535B1

(12) United States Patent
McCann

(10) Patent No.: US 8,551,535 B1
(45) Date of Patent: Oct. 8, 2013

(54) HOMEOPATHIC REMEDIES AND METHODS FOR ENHANCING WEIGHT LOSS

(76) Inventor: Sarah McCann, Chicago, IL (US)

( * ) Notice: Subject to any disclaimer, the term of this patent is extended or adjusted under 35 U.S.C. 154(b) by 0 days.

(21) Appl. No.: 13/567,459

(22) Filed: Aug. 6, 2012

(51) Int. Cl.
*A61K 33/10* (2006.01)
*A61K 33/06* (2006.01)

(52) U.S. Cl.
USPC .......... 424/715; 424/687; 424/725; 424/764; 424/776

(58) Field of Classification Search
USPC ........................................... 424/715
See application file for complete search history.

(56) References Cited

U.S. PATENT DOCUMENTS

| | | |
|---|---|---|
| 4,133,752 A | 1/1979 | Kurane et al. |
| 4,328,245 A | 5/1982 | Yu et al. |
| 4,358,603 A | 11/1982 | Yu |
| 4,409,239 A | 10/1983 | Yu |
| 4,410,545 A | 10/1983 | Yu et al. |
| 5,006,338 A | 4/1991 | Luenemann |
| 5,061,491 A | 10/1991 | Deryabin |
| 5,190,867 A | 3/1993 | Bertola et al. |
| 5,234,826 A | 8/1993 | Yamagami et al. |
| 5,326,702 A | 7/1994 | Endo et al. |
| 5,411,733 A | 5/1995 | Hozumi et al. |
| 5,571,794 A | 11/1996 | Frome |
| 5,667,995 A | 9/1997 | Whitehead |
| 5,939,288 A | 8/1999 | Thornburg |
| 5,980,870 A | 11/1999 | Baik et al. |
| 6,024,998 A | 2/2000 | Kreuter et al. |
| 6,126,942 A | 10/2000 | Yang |
| 6,207,164 B1 | 3/2001 | Kreuter et al. |
| 6,210,738 B1 | 4/2001 | Chen |
| 6,333,056 B1 | 12/2001 | Robinson |
| 6,426,098 B1 | 7/2002 | Yang, Jr. |
| 6,491,954 B2 | 12/2002 | Rifkin |
| 6,551,606 B1 | 4/2003 | Golz-Berner et al. |
| 7,011,853 B2 | 3/2006 | Ruepp |
| 7,026,529 B2 | 4/2006 | Ryu et al. |
| 7,037,532 B2 | 5/2006 | Foxman |
| 7,205,456 B2 | 4/2007 | Hallahan et al. |
| 7,416,743 B2 | 8/2008 | Tripathi |
| 7,540,438 B2 | 6/2009 | Buranov |
| 7,767,798 B2 | 8/2010 | Khanuja et al. |
| 7,943,169 B2 | 5/2011 | Domb et al. |
| 7,964,221 B2 | 6/2011 | Pylypchuk |
| 8,025,909 B2 | 9/2011 | Jarvis et al. |
| 2002/0076448 A1 | 6/2002 | Rifkin |
| 2003/0012824 A1 | 1/2003 | Ott et al. |
| 2003/0013639 A1 | 1/2003 | Yurchak et al. |
| 2004/0151688 A1 | 8/2004 | Sherbondy et al. |
| 2004/0166181 A1 | 8/2004 | Hegenauer et al. |
| 2004/0253326 A1 | 12/2004 | Mesko |
| 2005/0008710 A1 | 1/2005 | Subbiah |
| 2005/0032882 A1 | 2/2005 | Chen |
| 2005/0079247 A1 | 4/2005 | Slilaty |
| 2005/0084547 A1 | 4/2005 | Subbiah |
| 2005/0100513 A1 | 5/2005 | Watkins et al. |
| 2005/0142116 A1 | 6/2005 | Higuchi |
| 2005/0196465 A1 | 9/2005 | Foxman |
| 2006/0034825 A1 | 2/2006 | Charron |
| 2006/0045919 A1 | 3/2006 | Jonas |
| 2006/0147555 A1 | 7/2006 | Tripathi |
| 2007/0065456 A1 | 3/2007 | Woods |
| 2007/0077308 A1 | 4/2007 | Giner |
| 2007/0110676 A1 | 5/2007 | Clymer et al. |
| 2007/0123474 A1 | 5/2007 | Khanuja et al. |
| 2008/0038377 A1 | 2/2008 | Citow |
| 2008/0069906 A1 | 3/2008 | Thompson |
| 2008/0241288 A1 | 10/2008 | Thompson |
| 2008/0279902 A1* | 11/2008 | Luria et al. ............ 424/401 |
| 2008/0305096 A1 | 12/2008 | Verdegem et al. |
| 2009/0252796 A1 | 10/2009 | Mazed et al. |
| 2009/0297643 A1 | 12/2009 | Agarwal |
| 2010/0021533 A1 | 1/2010 | Mazed et al. |
| 2010/0021556 A1 | 1/2010 | Temper |
| 2010/0226863 A1 | 9/2010 | Piraino |
| 2010/0316737 A1 | 12/2010 | Farrington et al. |
| 2011/0020443 A1* | 1/2011 | Liu et al. ............ 424/464 |
| 2011/0038949 A1 | 2/2011 | Oswal et al. |
| 2011/0064778 A1 | 3/2011 | Moser et al. |
| 2011/0072575 A1 | 3/2011 | Cao |
| 2011/0117191 A1 | 5/2011 | Brondlund |
| 2011/0129552 A1 | 6/2011 | Saha et al. |
| 2011/0135747 A1 | 6/2011 | Polich |
| 2011/0135762 A1 | 6/2011 | Mortensen |
| 2011/0236358 A1 | 9/2011 | Sala |
| 2011/0236488 A1 | 9/2011 | Krishnan |
| 2011/0237552 A1 | 9/2011 | Heinemann et al. |

* cited by examiner

*Primary Examiner* — David J Blanchard
*Assistant Examiner* — John P Nguyen
(74) *Attorney, Agent, or Firm* — Whyte Hirschboeck Dudek S.C.

(57) ABSTRACT

Homeopathic compositions and formulations are disclosed. In one embodiment, compositions and formulations are disclosed that aid in weight loss and maintenance of a healthy weight. In another embodiment, methods are disclosed for producing homeopathic compositions and formulations. In still another embodiment, methods are disclosed for helping an individual lose weight.

14 Claims, No Drawings

HOMEOPATHIC REMEDIES AND METHODS FOR ENHANCING WEIGHT LOSS

FIELD

Embodiments disclosed herein relate to homeopathic compositions and formulations. In certain embodiments, methods are disclosed for producing homeopathic compositions and formulations. In yet another embodiment, methods are disclosed for using homeopathic compositions and formulations for weight loss.

BACKGROUND

The history of homeopathy dates back to the eighteenth century and the research of the German physician Samuel Hahnemann, who postulated the principle of "like cures like." In the nineteenth century, Hugo Paul Friedrich Schultz postulated that toxins can have the opposite effect in small doses compared to large doses. In 1888, Schultz showed that very low concentrations of yeast toxins increased yeast growth over 100 fold. At the same time, the psychiatrist Rudolph Arndt developed his "Basic Law of Biology," which states that weak stimuli slightly accelerate the vital activity, middle-strong stimuli raise it, strong stimuli suppresses it, and very strong stimuli halt vital activity. These separate observations were formulated by Arndt in 1888 into one of the earliest laws of pharmacology representing the homeopathic effect, the Arndt-Schultz rule, which states: every stimulus on a living cell elicits an activity, which is inversely proportional to the intensity of the stimulus. This law was later restated by Ferdinand Hueppe as: for every substance, small doses stimulate, moderate doses inhibit, and large doses kill.

Allopathic medicine, with its emphasis on moderate drug doses, works to inhibit undesired physical symptoms and to kill undesired pathogens. Homeopathic medicine, on the other hand, begins with small doses and moves towards progressively higher dilutions to stimulate the body's own natural electromagnetic forces. One of the basic tenets of homeopathic medicine is that a cure for a disease can be evoked by using a high dilution medicine that resembles, yet is different from, the cause of the disease.

Homeopathic mother tinctures are made following monographs laid down in the various homeopathic pharmacopoeias, for example German Homeopathic Pharmacopeia (G.H.P. or H.A.B.), European Pharmacopeia (E.P.), French Homeopathic Pharmacopeia, British Homeopathic Pharmacopeia (B.H.P.) or the Homeopathic Pharmacopeia of the United States (H.P.U.S.). While plants are the base ingredients for approximately 65% of homeopathic tinctures, the remaining 35% are made from many mineral, animal or imponderable substances. Thus, the production of a homeopathic tincture involves the use of base ingredients from x-ray to diamond to *Pulsatilla* (the Wind flower)

A homeopathic mother tincture, comprising base ingredients such as for example fresh plants, is generally prepared by extracting the ingredients in a suitable solvent, followed by the steps of comminution, maceration and squeezing according to accepted homeopathic pharmacopoeia. Suitable solvents include alcohol, water, water-alcohol mixtures, glycerine or isotonic sodium chloride solutions. Other techniques include tituration (grinding) with lactose to form a powdered dilution. Generally, herbal tinctures are prepared in a different manner generally involving the use of a solvent to extract the base ingredient without the maceration or grinding steps.

In use, the mother tincture or 1× potency ($1\times10^{-1}$ dilution) may be used as is, for example in diseases where the patient can benefit from the active principles within the tincture. This assumes that the base tincture is not of a toxic nature. Optionally, the mother tincture may be further diluted. Essentially, a series of dilutions are prepared from the base preparation or mother tincture. This step is called potentization and involves a series of dilutions. Between each series, the diluted substance is succussed (shaken in a vigorous manner). The process of dilution and succussion leads to a gradual loss of chemical toxicity while gradually increasing the homeopathic potency; the more dilute remedies being of greater potency.

Thus, homeopathic tinctures require a further dilution step in the production of the mother homeopathic tincture. This means that a homeopathic mother tincture is a 1× or 1 to 10 dilution of the base ingredient according to the HPUS. Additionally, it is important to note that it is not possible to reconstitute a herbal mother tincture from a homeopathic mother tincture. Thus, what makes a tincture truly homeopathic is the additional dilution process to where the final mother tincture represents a dilution of 1:10 of the base ingredient.

The dilution and succussion level of homeopathic drugs are denoted as "x," "X" or "d" for the decimal scale or centesimal "c," "C" scale or LM (Q) as 1:50,000 dilutions. This is explained in more detail in the table below.

| Decimal | | | Centesimal | | |
|---|---|---|---|---|---|
| POTENCY | DILUTION | CONCENTRATION | POTENCY | DILUTION | CONCENTRATION |
| 1× or D1 | 1:10 | $10^{-1}$ | 6c | $1:10^{12}$ | $1 \times 10^{-12}$ |
| 2× or D2 | 1:100 | $10^{-2}$ | 7c | $1:10^{14}$ | $1 \times 10^{-14}$ |
| 3× or D3 | 1:1000 | $10^{-3}$ | 11c | $1:10^{23}$ | $1 \times 10^{-23}$ |
| 4× or D4 | 1:10000 | $10^{-4}$ | 12c | $1:10^{24}$ | $1 \times 10^{-24}$ |
| 5× or D5 | 1:100000 | $10^{-5}$ | 30c | $1:10^{60}$ | |
| 6× or D6 | 1:1000000 | $10^{-6}$ | 200c | $1:10^{400}$ | |
| 30× or D30 | $1:10^{30}$ | $10^{-30}$ | 1M | $1:10^{2000}$ | |
| | | | 10M | $1:10^{20000}$ | |
| | | | LM1 (Q) | 3c diluted | 1:50,000 |

For example, for a "3×" preparation, the mother tincture is diluted with nine parts of the desired diluent, in either liquid or powder form. The resultant mixture is then diluted a second time, in a ratio of one part mixture to nine parts solvent and the resulting mixture is diluted a third time in the same manner. Therefore, the 3× or D3 potency is actually at $1\times10^{-3}$ (1/1000) of the mother tincture.

In the "C scale" each dilution is done with ninety-nine parts diluent to the original mixture. Therefore, a 3 C potency dilution is at $1\times10^{-6}$ potency of the original mixture. Ideally, X potency dilution is usually carried out with approximately 10 to 20 succussions, while C potency dilutions are also carried out with anywhere from 10 to 20 succussions. The more stages of dilution and succussion a homeopathic solution has undergone, the higher the potency of that remedy.

Critical reviews of more than 100 controlled and/or clinical studies of homeopathy show that patients received positive healing benefits from homeopathy beyond the placebo effect. Homeopathy is widely accepted as a useful therapeutic approach throughout Europe, N. America, the British Commonwealth countries, and India.

An estimated 50% of individuals in the United States are overweight. Moreover, an estimated 50% Of these individuals are sufficiently overweight to be considered obese. Obesity has been recognized as a public health problem in the United States, as well as the rest of the world.

Overweight or obese individuals are at higher risk for developing diseases such as hypertension, dyslipidemia, type-2 diabetes (non-insulin dependent diabetes mellitus or NIDDM), coronary heart disease, stroke, gallbladder diseases, osteoarthritis, sleep apnea, and respiratory problems. Such individuals also exhibit a higher prevalence of endometrial, breast, prostrate, and colon cancers. Further, higher than ideal body weight is associated with an increase in all causes of mortality.

The pharmaceutical industry is working diligently to develop drugs to help people lose weight. However, the drug products available to the general public, whether by prescription or as over-the-counter preparations, are not free of risk. Such risks are not limited to prescription and/or over-the-counter medications. The use of ephedra in nutritional products employed for weight loss has been associated with numerous incidences of arrhythmia in susceptible individuals taking such preparations.

Therefore, it would be useful to identify compositions and formulations that help individuals lose weight and alleviate the discomforts of dieting. There is a need for less expensive, safer and more user-friendly compositions and formulations for use in the treatment of a wide variety of conditions. Hence, specific homeopathic complexes are disclosed that can treat a wide number of disorders without serious negative side effects and the cost issues usually associated with conventional pharmaceuticals.

BRIEF SUMMARY

In one embodiment, a composition is disclosed comprising a homeopathic tincture or dilutions thereof of *nux vomica*; calcarea carbonicum; magnesium phosphoricum; and *taraxacum*.

In another embodiment, compositions are disclosed that can alleviate the discomforts of dieting.

In still another embodiment, methods for alleviating the discomforts of dieting are disclosed.

In another embodiment, methods are disclosed for using a homeopathic complex as defined herein for treatment of disease. In one embodiment, the disease is obesity.

In still another embodiment, methods are disclosed for treating a disease comprising administering to a subject in need thereof an effective amount of a homeopathic complex as defined herein.

An advantage of the compositions and methods disclosed herein is a homeopathic formulation that is stable.

An advantage of the compositions and methods disclosed herein is a homeopathic formulation that is non-toxic.

An advantage of the compositions and methods disclosed herein is a homeopathic formulation that is free of serious side effects.

An advantage of the compositions and methods disclosed herein is a homeopathic formulation that is easy to prepare.

An advantage of the compositions and methods disclosed herein is a homeopathic formulation that can be combined with other homeopathic preparations to achieve desirable effects.

An advantage of the compositions and methods disclosed herein is a homeopathic formulation that is compatible with conventional methods of treatment and other therapies.

An advantage of the compositions and methods disclosed herein is a homeopathic formulation that is cost-effective.

DETAILED DESCRIPTION

Definitions

The numerical ranges in this disclosure are approximate, and thus may include values outside of the range unless otherwise indicated. Numerical ranges include all values from and including the lower and the upper values, in increments of one unit, provided that there is a separation of at least two units between any lower value and any higher value. As an example, if a compositional, physical or other property, such as, for example, molecular weight, viscosity, etc., is from 100 to 1,000, it is intended that all individual values, such as 100, 101, 102, etc., and sub ranges, such as 100 to 144, 155 to 170, 197 to 200, etc., are expressly enumerated. For ranges containing values which are less than one or containing fractional numbers greater than one (e.g., 1.1, 1.5, etc.), one unit is considered to be 0.0001, 0.001, 0.01 or 0.1, as appropriate. For ranges containing single digit numbers less than ten (e.g., 1 to 5), one unit is typically considered to be 0.1. These are only examples of what is specifically intended, and all possible combinations of numerical values between the lowest value and the highest value enumerated, are to be considered to be expressly stated in this disclosure. Numerical ranges are provided within this disclosure for, among other things, relative amounts of components in a mixture, and various temperature and other parameter ranges recited in the methods.

As used herein, the terms "tincture" and "homeopathic preparation" of an ingredient refer to extracts of a part, combinations of parts and/or the entirety of the ingredient. The "tincture" can be prepared by exposing a part; parts and/or the entirety of the ingredient in a solvent, e.g. alcohol and/or water. The "tincture" of an ingredient preferably is a mother tincture of the ingredient prepared according to the procedures in the Homeopathic Pharmacopeia of the United States (HPUS).

The "homeopathic preparation" can be prepared by dilution of the "tincture" with an appropriate liquid such as water or alcohol. The "homeopathic preparation" of an ingredient for the formulation disclosed herein is preferably prepared as per HPUS procedures, wherein the mother tincture of the ingredient is serially diluted and subjected to succussion according to the target potency using potentization procedures known in the art of homeopathy.

As used herein, the term "potency" of a homeopathic remedy refers to how many times it has undergone the process of serial dilution and succussion (known as "potentization"), and therefore how far it has been removed from a crude or material form. This process is carried out according to a number of different scales: Decimal, Centessimal and Fifty-Millessimal.

For decimal scale (1:10), which is referred to as "D Potencies" (for "Decimal"), or "X Potencies," one part of the original liquid substance is added to 9 parts of a carrier such as alcohol, and succussed (shaken vigorously) 10 times. The resulting product is referred to as a "D1" or "1×." One part of this is then added to 9 parts of alcohol and succussed 10 times, resulting in a D2 (2×) and so on. A medicine subjected to this process 30 times will thus be called a D30 (30×).

For potentization of non-liquid substances, the process is done using a carrier of milk-sugar rather than alcohol, and triturated rather than succussed. Once a dilution ratio of 1:1,000,000 (6× or D6) has been reached, the insoluble substance is then rendered soluble, and preparation can be continued in a liquid medium as described above.

For centessimal scale (1:100), which is referred to as "C Potencies" (for "Centessimal"), one part of the original liquid substance is added to 99 parts of a carrier such as alcohol, and succussed (shaken vigorously) 10 times. The resulting product is referred to as a "C1" or "1C." One part of this is then added to 99 parts of alcohol and succussed 10 times, resulting in a 2C and so on. A medicine subjected to this process 30 times will thus be called 30C, 200 times will be called 200C and so on. For the sake of ease in labeling, at higher potencies the numbers are dropped in favor of Roman numerals. For example 1000C is shortened to 1M (M=Millessimal, or 1000), 10,000C=10M, 50,000C=50M, 100,000C=CM, 1,000,000C=MM and the like.

For potentization of non-liquid substances, the process is done using a carrier of milk-sugar rather than alcohol, and triturated rather than successed. Once a dilution ratio of 1:1,000,000 (3c) has been reached, the insoluble substance is then rendered soluble, and preparation can be continued in a liquid medium, as described above.

As used herein, the term "succession" refers to vigorous shaking of a diluted homeopathic preparation in order to activate the medicinal substance.

As used herein, the term "trituration" is the process for reducing the particle size of a substance by grinding, as by grinding of powders in a mortar with a pestle.

I. Homeopathic Composition

In one embodiment, homeopathic compositions and formulations are disclosed. In yet another embodiment, a homeopathic tincture or dilutions thereof is disclosed comprising two or more of the following: *nux vomica* or other remedy with a similar profile; calcarea carbonicum or other similar profiled calcarea; magnesium phosphoricum or other similar profiled magnesium; and *taraxacum* or other remedy with a similar profile.

In still another embodiment, a homeopathic composition is disclosed comprising three or more of the following *nux vomica* or other remedy with a similar profile; calcarea carbonicum or other similar profiled calcarea; magnesium phosphoricum or other similar profiled magnesium; and *taraxacum* or other remedy with a similar profile.

In another embodiment, a homeopathic composition is disclosed comprising *nux vomica* or other remedy with a similar profile; calcarea carbonicum or other similar profiled calcarea; magnesium phosphoricum or other similar profiled magnesium; and *taraxacum* or other remedy with a similar profile.

In yet another embodiment, a homeopathic composition is disclosed comprising *nux vomica;* calcarea carbonicum; magnesium phosphoricum; and *taraxacum*.

In one embodiment, the composition is effective in maintaining a healthy lifestyle and maintaining a healthy weight. In another embodiment, the compositions disclosed herein are useful for promoting weight loss.

In one embodiment, the components of the composition are in the form of tincture. In yet another embodiment, each of the components is potentized. In still another embodiment, the components are in the form of aqueous extracts. In another embodiment, the components are in the form of ethanolic solutions.

In another embodiment, the components have a potency ranging from tincture to all X, C and LM (1:50,000 dilution ratio) potencies and above, preferably ranging from about 3° C. to about 1 M.

In yet another embodiment, the potencies may either be 'X' potencies or 'C' potencies.

In still another embodiment, the composition is mixed with a carrier. In another embodiment, the carrier is a physiologically acceptable carrier selected from a group consisting of whey, sucrose, calcium carbonate, microcrystalline cellulose, carbon, carnauba wax, croscarmellose sodium, stearic acid, magnesium stearate, silicon dioxide and ethanol.

In yet another embodiment, the proportion of each of the components ranges from about 1:1 to about 1:10 with respect to each other component.

In another embodiment, the composition is in a form selected from the group consisting of solution, syrup, elixir, suspension, emulsion, tablets, capsules, powders, globules, lozenges, pills, and pellets.

In still another embodiment, the compositions disclosed herein may be combined with other treatment methods and substances including allopathic medicines, vitamins, minerals, amino acids, traditional homeopathic remedies, inert substances, etc. The individual components may be given in potentized forms and also in other forms such as, but not limited to, mother tincture, biotechnology form, nanotechnology form, etc.

In another embodiment, the individual components of the composition may be administered all together at the same time and/or in various permutations and combinations. For example, a few ingredients could be administered together at one time, and the others at a different time; etc. Additional components could be added to the treatment that could increase its effectiveness or allow it to function with the same level of effectiveness.

In one embodiment, compositions disclosed herein can be used to help individuals lose weight. In another embodiment, compositions disclosed herein can be used to help individuals achieve a healthy weight. Such an effect can be assessed and measured objectively by comparing the amount of weight lost with and without the administration of the compositions disclosed herein. For instance, individuals can be split into two groups, with each group receiving the same number of calories. One group is administered the homeopathic composition and the other group is not. The amount and percentage of weight lost for each individual can be tracked. After a suitable period of time, for example 60 days, the amount and percentage of weight lost for each group can be compared.

Table I lists certain remedies relevant to the compositions disclosed herein.

| Name of Remedy | Abbreviation | Alternative nomenclature |
| --- | --- | --- |
| Calcarea carbonica | Calc | Calc Carb |
| | | Calcarea carbonica |
| | | Calcarea |
| | | Conchae Praeparatae |
| | | Impure Calcium Carbonate |
| | | Ostrearum |
| Nux vomica | Nux-v | N.O. loganiaceae |
| | | Nux |
| | | Nux vomica |
| | | Poison nut |
| | | Strychonos |
| *Taraxacum officinale* | Tarax | Dandelion |
| | | *Leontodum taraxacum* |
| | | N. O. Compositae |
| | | *Taraxacum* |

A. Components

1. *Nux Vomica*

The strychnine tree (*Strychnos nux-vomica* L.) also known as *nux vomica*, poison nut, semen *strychnos* and quaker buttons, is a deciduous tree native to India and southeast Asia. It is a medium-sized tree in the family Loganiaceae that grows in open habitats.

It is a major source of the highly poisonous alkaloids strychnine and brucine, derived from the seeds inside the tree's round, green to orange fruit. The seeds contain approximately 1.5% strychnine, and the dried blossoms contain 1.0%. However, the tree's bark also contains brucine and other poisonous compounds.

*Nux Vomica* contains the alkaloids, Strychnine and Brucine, also traces of strychnicine, and a glucoside Loganin, about 3 percent fatty matter, caffeotannic acid and a trace of copper. The pulp of the fruit contains about 5 percent of loganin together with the alkaloid strychnicine.

The properties of *Nux Vomica* are substantially those of the alkaloid Strychnine. The tincture of *Nux Vomica* may be used in mixtures—for its stimulant action on the gastro-intestinal tract. In the mouth, it acts as a bitter, increasing appetite; it stimulates peristalsis, in chronic constipation due to atony of the bowel it is often combined with cascara and other laxatives with good effects.

Strychnine, the chief alkaloid constituent of the seeds, also acts as a bitter increasing the flow of gastric juice. It is rapidly absorbed as it reaches the intestines, and exerts characteristic effects upon the central nervous system: the movements of respiration are deepened and quickened and the heart slowed through excitation of the vagal centre. The senses of smell, touch, hearing and vision are rendered more acute.

In addition, it improves the pulse and raises blood pressure and is of great value as a tonic to the circulatory system in cardiac failure. Strychnine is excreted very slowly and its action is cumulative in any but small doses.

In one embodiment, a remedy with a similar profile to *nux vomica* may be used. The homeopathic composition can comprise *nux vomica* and one or more additional remedies with a similar profile to *nux vomica*. Any number of additional remedies with a similar profile to *nux vomica* can be used including but not limited to 2, 3, 4, 5, 6, 7, 8, 9, 10, 11-20, 21-30, 31-40, 41-50, and greater than 50 remedies with a similar profile to *nux vomica*.

*Nux vomica* can be in any suitable potency including but not limited to 6x to 1M.

In one embodiment, *nux vomica* has a potency of 6c.

2. *Taraxacum*

*Taraxacum* is a large genus of flowering plants in the family Asteraceae. They are native to Eurasia and North America, and two species, *T. officinale* and *T. erythrospermum*, are found as weeds worldwide. Both species are edible in their entirety. The common name is dandelion.

The Dandelion (*Taraxacum officinale*, Weber, *T. Densleonis*, Desf; *Leontodon taraxacum*, Linn.), though not occurring in the Southern Hemisphere, is at home in all parts of the north temperate zone, in pastures, meadows and on waste ground, and is so plentiful that farmers everywhere find it a troublesome weed, for though its flowers are more conspicuous in the earlier months of the summer, it may be found in bloom, and consequently also prolifically dispersing its seeds, almost throughout the year.

The chief constituents of Dandelion root are Taraxacin, acrystalline, bitter substance, of which the yield varies in roots collected at different seasons, and Taraxacerin, an acrid resin, with Inulin (a sort of sugar which replaces starch in many of the Dandelion family, Compositae), gluten, gum and potash. The root contains no starch, but early in the year contains much uncrystallizable sugar and laevulin, which differs from Inulin in being soluble in cold water. This diminishes in quantity during the summer and becomes Inulin in the autumn. The root may contain as much as 24 percent inulin. In the fresh root, the Inulin is present in the cell-sap, but in the dry root it occurs as an amorphodus, transparent solid, which is only slightly soluble in cold water, but soluble in hot water.

The genus is taxonomically complex, with some botanists dividing the group into about 34 macrospecies, and about 2000 microspecies; approximately 235 apomictic and polyploid microspecies have been recorded in Great Britain and Ireland. Some botanists take a much narrower view and only accept a total of about 60 species. Representative species are recited below:

*Taraxacum albidum*, a white-flowering Japanese dandelion;

*Taraxacum californicum*, the endangered California dandelion;

*Taraxacum japonicum*, Japanese dandelion. No ring of smallish, downward-turned leaves under the flowerhead;

*Taraxacum kok-saghyz*, Russian dandelion, which produces rubber;

*Taraxacum laevigatum*, Red-seeded Dandelion; achenes reddish brown and leaves deeply cut throughout length. Inner bracts' tips are hooded;

*Taraxacum erythrospermum*, often considered a variety of *Taraxacum laevigatum*; and

*Taraxacum officinale* (syn. *T. officinale* subsp. *vulgare*), Common Dandelion. Found in many forms.

In one embodiment, a remedy with similar profile to *taraxacum* can be used. The homeopathic composition can comprise *taraxacum* and one or more additional remedies with a similar profile to *taraxacum*. Any number of additional remedies with a similar profile to *taraxacum* can be used including but not limited to 2, 3, 4, 5, 6, 7, 8, 9, 10, 11-20, 21-30, 31-40, 41-50, and greater than 50 remedies with a similar profile to *taraxacum*.

In one embodiment, *taraxacum* from any member of the *taraxacum* genus may be used including any macrospecies or microspecies. Two or more than two *taraxacum* family members may be used in combination including but not limited to 3, 4, 5, 6, 7, 8, 9, 10, 11-20, 21-30, 31-40, 41-50, and greater than 50 *taraxacum* family members.

*Taraxacum* can be in any suitable potency including but not limited to 6x to 1 M.

In one embodiment, *taraxacum* has a potency of 6x.

3. Calcarea Carbonica

Calcarea carbonica (calcium carbonate) is a chemical compound with the formula $CaCO_3$. It is a common substance found in rocks in all parts of the world, and is the main component of shells of marine organisms, snails, coal balls, pearls, and eggshells. Calcium carbonate is the active ingredient in agricultural lime. It is commonly used medicinally as a calcium supplement or as an antacid, but excessive consumption can be hazardous.

The vast majority of calcium carbonate used in industry is extracted by mining or quarrying. Pure calcium carbonate (e.g. for food or pharmaceutical use), can be produced from a pure quarried source (usually marble).

Alternatively, calcium carbonate is prepared by calcining crude calcium oxide. Water is added to give calcium hydroxide, and carbon dioxide is passed through this solution to precipitate the desired calcium carbonate, referred to in the industry as precipitated calcium carbonate (PCC):

$$CaCO_3 \rightarrow CaO + CO_2$$

$$CaO + H_2O \rightarrow Ca(OH)_2$$

$$Ca(OH)_2 + CO_2 \rightarrow CaCO_3 + H_2O$$

Calcium carbonate is found naturally as the following minerals in the form of polymorphs: aragonite; calcite; and Vaterite or ($\mu$-$CaCO_3$). The trigonal crystal structure of calcite is most common.

The calcium carbonate minerals occur in the following rocks: chalk; limestone; marble; and travertine.

In one embodiment, a remedy with similar profile to calcarea carbonica can be used. The homeopathic composition can comprise calcarea carbonica and one or more additional remedies with a similar profile to calcarea carbonica. Any number of additional remedies with a similar profile to calcarea carbonica can be used including but not limited to 2, 3, 4, 5, 6, 7, 8, 9, 10, 11-20, 21-30, 31-40, 41-50, and greater than 50 remedies with a similar profile to calcarea carbonica.

Calcarea carbonica can be in any suitable potency including but not limited to 6× to 1M.

In one embodiment, calcarea carbonica has a potency of 6c.

4. Magnesium Phosphoricum

Magnesium phosphoricum ($Mg\ HPO_4\ 7H_2O$) is made by mixing phosphate of soda with sulphate of magnesia. The crystals resulting are six-sided, needle-like. They have a cooling, sweetish taste. They are sparingly soluble in water; 322 parts dissolving one part after standing a long time. Boiling decomposes magnesium phosphoricum. It exists in the grains of cereals, and can be detected in considerable quantity in beer.

Magnesium phosphoricum is an earthy constituent of muscles, nerves, bone, brain, (grey substance much more) spine, sperma (especially rich in Magnes. phos.), teeth and blood corpuscles. Magnesium phosphoricum is used as an anti-spasmodic remedy.

In one embodiment, a remedy with similar profile to magnesium phosphoricum can be used. The homeopathic composition can comprise magnesium phosphoricum and one or more additional remedies with a similar profile to magnesium phosphoricum. Any number of additional remedies with a similar profile to magnesium phosphoricum can be used including but not limited to 2, 3, 4, 5, 6, 7, 8, 9, 10, 11-20, 21-30, 31-40, 41-50, and greater than 50 remedies with a similar profile to magnesium phosphoricum.

In one embodiment, the similar remedy is *matricaria recutita*.

Magnesium phosphoricum can be in any suitable potency including but not limited to 6× to 1M.

In one embodiment, magnesium phosphoricum has a potency of 6c.

B. Formulations for Oral Administration

Oral pharmaceutical dosage forms may be as a solid, gel or liquid. Examples of solid dosage forms include, but are not limited to pillules, tablets, capsules, granules, and bulk powders. More specific examples of oral tablets include compressed, chewable lozenges and tablets that may be enteric-coated, sugar-coated or film-coated. Examples of capsules include hard or soft gelatin capsules. Granules and powders may be provided in non-effervescent or effervescent forms. Each may be combined with other ingredients known to those skilled in the art.

In certain embodiments, compounds according to the disclosure are provided as solid dosage forms, preferably capsules or tablets. The tablets, pillules, capsules, troches and the like may optionally contain one or more of the following ingredients, or compounds of a similar nature: a binder; a diluent; a disintegrating agent; a lubricant; a glidant; a sweetening agent; and a flavoring agent.

Examples of binders that may be used include, but are not limited to, microcrystalline cellulose, gum tragacanth, glucose solution, acacia mucilage, gelatin solution, sucrose, and starch paste.

Examples of lubricants that may be used include, but are not limited to, talc, starch, magnesium or calcium stearate, *lycopodium* and stearic acid.

Examples of diluents that may be used include, but are not limited to, lactose, sucrose, starch, kaolin, salt, mannitol, and dicalcium phosphate.

Examples of glidants that may be used include, but are not limited to, colloidal silicon dioxide.

Examples of disintegrating agents that may be used include, but are not limited to, crosscarmellose sodium, sodium starch glycolate, alginic acid, corn starch, potato starch, bentonite, methylcellulose, agar and carboxymethylcellulose.

Examples of coloring agents that may be used include, but are not limited to, any of the approved certified water-soluble FD and C dyes, mixtures thereof, and water insoluble FD and C dyes suspended on alumina hydrate.

Examples of sweetening agents that may be used include, but are not limited to, sucrose, lactose, mannitol and artificial sweetening agents such as sodium cyclamate and saccharin, and any number of spray-dried flavors.

Examples of flavoring agents that may be used include, but are not limited to, natural flavors extracted from plants such as fruits and synthetic blends of compounds that produce a pleasant sensation, such as, but not limited to peppermint and methyl salicylate.

Examples of wetting agents that may be used include, but are not limited to, propylene glycol monostearate, sorbitan monooleate, diethylene glycol monolaurate, and polyoxyethylene lauryl ether.

Examples of anti-emetic coatings that may be used include, but are not limited to, fatty acids, fats, waxes, shellac, ammoniated shellac and cellulose acetate phthalates.

Examples of film coatings that may be used include, but are not limited to, hydroxyethylcellulose, sodium carboxymethylcellulose, polyethylene glycol 4000 and cellulose acetate phthalate.

If oral administration is desired, the salt of the compound may optionally be provided in a composition that protects it from the acidic environment of the stomach. For example, the composition can be formulated in an enteric coating that maintains its integrity in the stomach and releases the active compound in the intestine. The composition may also be formulated in combination with an antacid or other such ingredient.

When the dosage unit form is a capsule, it may optionally additionally comprise a liquid carrier such as a fatty oil. In addition, dosage unit forms may optionally additionally comprise various other materials that modify the physical form of the dosage unit, for example, coatings of sugar and other enteric agents.

Compositions and formulations according to the disclosure may also be administered as a component of an elixir, suspension, syrup, wafer, sprinkle, chewing gum or the like. A syrup may optionally comprise, in addition to the active compounds, sucrose as a sweetening agent and certain preservatives, dyes and colorings and flavors.

Compositions and formulations may also be mixed with other active materials that do not impair the desired action, or with materials that supplement the desired action, such as antacids, H2 blockers, and diuretics. For example, if a compound is used for treating asthma or hypertension, it may be used with other bronchodilators and antihypertensive agents, respectively.

Examples of pharmaceutically acceptable carriers that may be included in tablets comprising compounds of the present disclosure include, but are not limited to binders, lubricants, diluents, disintegrating agents, coloring agents, flavoring agents, and wetting agents. Enteric-coated tablets, because of the enteric-coating, resist the action of stomach acid and dissolve or disintegrate in the neutral or alkaline intestines. Sugar-coated tablets may be compressed tablets to which different layers of pharmaceutically acceptable substances are applied. Film-coated tablets may be compressed tablets that have been coated with polymers or other suitable coating. Multiple compressed tablets may be compressed tablets made by more than one compression cycle utilizing the pharmaceutically acceptable substances previously mentioned. Coloring agents may also be used in tablets. Flavoring and sweetening agents may be used in tablets, and are especially useful in the formation of chewable tablets and lozenges.

Examples of liquid oral dosage forms that may be used include, but are not limited to, aqueous solutions, emulsions, suspensions, solutions and/or suspensions reconstituted from non-effervescent granules and effervescent preparations reconstituted from effervescent granules.

Examples of aqueous solutions that may be used include, but are not limited to, elixirs and syrups. As used herein, elixirs refer to clear, sweetened, hydroalcoholic preparations. Examples of pharmaceutically acceptable carriers that may be used in elixirs include, but are not limited to solvents. Particular examples of solvents that may be used include glycerin, sorbitol, ethyl alcohol and syrup. As used herein, syrups refer to concentrated aqueous solutions of a sugar, for example, sucrose. Syrups may optionally further comprise a preservative.

Emulsions refer to two-phase systems in which one liquid is dispersed in the form of small globules throughout another liquid. Emulsions may optionally be oil-in-water or water-in-oil emulsions. Examples of pharmaceutically acceptable carriers that may be used in emulsions include, but are not limited to non-aqueous liquids, emulsifying agents and preservatives.

Examples of pharmaceutically acceptable substances that may be used in non-effervescent granules, to be reconstituted into a liquid oral dosage form, include diluents, sweeteners and wetting agents.

Examples of pharmaceutically acceptable substances that may be used in effervescent granules, to be reconstituted into a liquid oral dosage form, include organic acids and a source of carbon dioxide.

Coloring and flavoring agents may optionally be used in all of the above dosage forms.

Particular examples of preservatives that may be used include glycerin, methyl and propylparaben, benzoic add, sodium benzoate and alcohol.

Particular examples of non-aqueous liquids that may be used in emulsions include mineral oil and cottonseed oil.

Particular examples of emulsifying agents that may be used include gelatin, acacia, tragacanth, bentonite, and surfactants such as polyoxyethylene sorbitan monooleate.

Particular examples of suspending agents that may be used include sodium carboxymethylcellulose, pectin, tragacanth, Veegum and acacia. Diluents include lactose and sucrose. Sweetening agents include sucrose, syrups, glycerin and artificial sweetening agents such as sodium cyclamate and saccharin.

Particular examples of wetting agents that may be used include propylene glycol monostearate, sorbitan monooleate, diethylene glycol monolaurate, and polyoxyethylene lauryl ether.

Particular examples of organic acids that may be used include citric and tartaric acid.

Sources of carbon dioxide that may be used in effervescent compositions include sodium bicarbonate and sodium carbonate. Coloring agents include any of the approved certified water soluble FD and C dyes, and mixtures thereof.

Particular examples of flavoring agents that may be used include natural flavors extracted from plants such fruits, and synthetic blends of compounds that produce a pleasant taste sensation.

For a solid dosage form, the solution or suspension, in for example propylene carbonate, vegetable oils or triglycerides, is preferably encapsulated in a gelatin capsule. Such solutions, and the preparation and encapsulation thereof, are disclosed in U.S. Pat. Nos. 4,328,245; 4,409,239; and 4,410,545. For a liquid dosage form, the solution, e.g., for example, in a polyethylene glycol, may be diluted with a sufficient quantity of a pharmaceutically acceptable liquid carrier, e.g., water, to be easily measured for administration.

Alternatively, liquid or semi-solid oral formulations may be prepared by dissolving or dispersing the active compound or salt in vegetable oils, glycols, triglycerides, propylene glycol esters (e.g., propylene carbonate) and other such carriers, and encapsulating these solutions or suspensions in hard or soft gelatin capsule shells. Other useful formulations include those set forth in U.S. Pat. No. 4,358,603.

II. Methods of Making Components of the Composition

A. Methods of Making *Nux vomica* for Homeopathic Compositions

One of ordinary skill in the art will understand there are numerous methods for the preparation and storage of *Nux Vomica*. A representative method is produced below.

1. Methodology for Liquid Potencies from Mother Tincture Stock

The HPUS uses mother tinctures of 1 in 10 drug strength. The first dilution (1c) is made with the same ethanolic concentration as the mother tincture. See HPUS monograph.

2. Preparation of 1c—HPUS Method Class C

One milliliter (1.0 ml) of tincture (1×) is succussed with nine milliliters (9.0 ml) of diluent to produce ten milliliters (10.0 ml) of 1C attenuation. The solution is succussed firmly.

3. Preparation of 5c

One milliliter (1.0 ml) of 1C attenuation is succussed with 99.0 ml of diluent to produce 100.0 ml of 2C attenuation. Subsequent attenuations are prepared by succussing 1.0 ml of the preceding attenuation with 99.0 ml of diluent to produce 100.0 ml of the succeeding attenuation up to the 5c level. Dispensing 90% alcohol is the specified menstruum for the final decimal or centesimal attenuation when intended for medicating purposes.

When homeopathic solutions are intended for oral or sublingual administration in liquid form, the final attenuation may be prepared with an appropriate percentage of alcohol alcohol at 60 percent v/v: for the 1c attenuation obtained from a tincture when appropriate;

alcohol at a minimum of 20 percent v/v: for the other attenuations.

B. Methods of Making Calcarea Carbonicum for Homeopathic Compositions

One of ordinary skill in the art will understand there are numerous methods for the preparation and storage of calcarea carbonicum. A representative method is produced below.

1. Trituration to 3c—HPUS method CLASS F

Weigh 0.06 g (1 part) of the original substance (inner part of the broken shells of the oyster *Ostrea edulis*) and place it in a brand new, well prepared mortar.

Add 1.98 g (33 parts) of Lactose BP and grind with the pestle firmly and steadily for a suitable period of time, about 6 minutes.

Scrape down the pestle head and the mortar, for 4 minutes with the spatula, to keep the powder flowing well. Resume grinding for 6 minutes then repeat the 4 minutes of scraping.

The spatula is placed on a clean sheet of paper towel which is replaced with a fresh one before each addition of lactose.

Another 1.98 g of lactose is added and the twenty minute cycle of two grindings and two scrapings is repeated. The last 1.98 g is then added, again with the same 20 minute cycle whereupon the 1c is completed.

The mortar and pestle are washed and treated. The 2c powder is prepared by repeating the above procedure using 0.06 g of the 1c powder as the starting point.

The 3c powder is prepared by repeating the above procedure using 0.06 g of the 2c powder as the starting point.

2. From 3c Trituration Powder to 4c Liquid Potency. HPUS Method CLASS H

Dissolve 0.06 g of 3c powder in 3.0 ml of distilled water with very gentle shaking. When completely dissolved, 3.0 ml of 90% ethanol is added and the solution succussed firmly with twenty strokes of the arm. This is then labelled 4c.

3. From 4c to 5c

One drop of this solution is added to 99 drops (3.4 ml) of 90% ethanol from the dispenser and succussed to create 3.4 ml 5c.

C. Methods of Making Magnesium Phosphoricum or Homeopathic Compositions

One of ordinary skill in the art will understand there are numerous methods for the preparation and storage of calcarea carbonicum. A representative method is produced below.

1. Trituration to 3c—HPUS Method CLASS F

Weigh 0.06 g (1 part) of the original substance and place it in a brand new, well prepared mortar. Add 1.98 g (33 parts) of Lactose BP and grind with the pestle firmly and steadily for 6 minutes. Scrape down the pestle head and the mortar, for 4 minutes with the spatula, to keep the powder flowing well.

Resume grinding for 6 minutes then repeat the 4 minutes of scraping. The spatula is placed on a clean sheet of paper towel which is replaced with a fresh one before each addition of lactose. Another 1.98 g of lactose is added and the twenty minute cycle of two grindings and two scrapings is repeated. The last 1.98 g is then added, again with the same 20 minute cycle whereupon the 1c is completed.

The mortar and pestle are washed and treated. The 2c powder is prepared by repeating the above procedure using 0.06 g of the 1c powder as the starting point. The 3c powder is prepared by repeating the above procedure using 0.06 g of the 2c powder as the starting point. The mortar and pestle are washed and treated.

2. From 3c Trituration Powder to 4c Liquid Potency. HPUS Method CLASS H

Dissolve 0.06 g of 3c powder in 3.0 ml of distilled water with very gentle shaking. When completely dissolved, 3.0 ml of 90% ethanol is added and the solution succussed firmly. This is then labeled 4c.

3. From 4c to 5c

One drop of this solution is added to 99 drops (3.4 ml) of 90% ethanol from the dispenser and succussed to create 3.4 ml 5c.

D. Methods of Making *Taraxacum* for Homeopathic Compositions

One of ordinary skill in the art will understand there are numerous methods for the preparation and storage of *taraxacum*. A representative method is produced below.

1. Methodology for Liquid Potencies from Mother Tincture Stock

The HPUS use mother tinctures of 1 in 10 drug strength. The first dilution (1c) is made with the same ethanolic concentration as the mother tincture. See HPUS monograph.

2. Preparation of 1c—HPUS method Class C

One milliliter (1.0 ml) of tincture (1×) is succussed with nine milliliters (9.0 ml) of diluent to produce ten milliliters (10.0 ml) of 2× attenuation. The solution is succussed firmly.

3. Preparation of 5×

One milliliter (1.0 ml) of 1C attenuation is succussed with 9.0 ml of diluent to produce 10.0 ml of 2× attenuation. Subsequent attenuations are prepared by succussing 1.0 ml of the preceding attenuation with 9.0 ml of diluent to produce 10.0 ml of the succeeding attenuation up to the 5× level.

Dispensing 90% alcohol is the specified menstruum for the final decimal or centesimal attenuation when intended for medicating purposes.

When homeopathic solutions are intended for oral or sublingual administration in liquid form, the final attenuation may be prepared with an appropriate percentage of alcohol:

alcohol at 60 percent v/v: for the 1c attenuation obtained from a tincture when appropriate;

alcohol at a minimum of 20 percent v/v: for the other attenuations.

III. Methods for Alleviating the Discomforts of Dieting

In another embodiment, methods for alleviating the discomforts of dieting are disclosed. In some embodiment, the method comprises administering a homeopathic composition as described above. In still another embodiment, the method comprises administering to an individual a composition comprising two or more of the following remedies: *nux vomica, taraxacum*, magnesium phosphoricum and calcarea carbonicum. In yet another embodiment, the method comprises administering to an individual three or more of the following remedies: *nux vomica, taraxacum*, magnesium phosphoricum and calcarea carbonicum. Such an effect can be assessed and measured subjectively by interviewing and questioning the individual about the discomforts associated with caloric restrictions before and after administration of the homeopathic compositions.

The discomforts of dieting include but are not limited to hunger; cravings for foods and/or alcohol; withdrawal symptoms such as anxiety, dizziness, jitters, cranky, and headaches; sleep problems; low energy; headaches from lessening food intake; leg cramps and achiness; slow weight loss; and bloating and gassy.

Administration of a homeopathic composition as described herein can help to alleviate the discomforts of dieting. Not to be bound by a specific theory or limited to the recited effects of the listed remedies, it is believed that the following remedies bring forth the following effects:

*Taraxacum*: alleviates gastric headaches and slow digestive tract; acts as a liver tonic (once your liver is healthier it may operate more optimally); helps clear up and alleviate flatulence.

Calcarea Carbonica: weight loss success; calms anxiety attacks that are associated with dieting and the feelings that you are suffering; relieves bloating.

Magnesium Phosphoricum: helps with the leg cramping that is associated with dieting; especially with people over 50 years old; helps boost energy

*Nux Vomica*: helps with irritability, withdrawal symptoms; helps calm cravings for food and/or alcohol; overall calming influence.

In another embodiment, methods for losing weight are disclosed. In still another embodiment, methods for achieving a healthy weight are disclosed.

In yet another embodiment, methods for losing weight comprise administering to an individual a homeopathic composition as disclosed herein and restricting the caloric intake of the individual. In one embodiment, the homeopathic composition comprises two or more of the following remedies: *nux vomica, taraxacum*, magnesium phosphoricum and calcarea carbonicum.

In another embodiment, homeopathic compositions disclosed herein are administered before consumption of a meal. In yet another embodiment, the homeopathic composition is administered about 5-15 minutes before the meal; about 15-30 minutes before the meal; 30-45 minutes before the meal; 45-60 minutes before the meal; 1-2 hours before the meal; 2-3 hours before the meal; and 3-6 hours before the meal.

In still another embodiment, the homeopathic composition is administered as soon as the individual is awakened. In yet another embodiment, the homeopathic composition is administered before the individual retires for the evening.

In another embodiment, restricting caloric intake includes but is not limited to 450-500, 500-550, 550-600, 600-650, 650-700, 700-750, 750-800, 800-850, 850-900, 900-950, 950-1000, 1000-1200, 1200-1500, 1500-1800, and 1800-2000 calories.

In yet another embodiment, restricting caloric intake comprises eating two meals and two snacks each day. Each meal consists of 4-6 ounces of protein; 1 cup of vegetable; unlimited salad greens; 1 fruit serving; and 1 bread or crunch serving.

The invention is now described with reference to the following Examples. These Examples are provided for the purpose of illustration only and the invention should in no way be construed as being limited to these Examples, but rather should be construed to encompass any and all variations that become evident as a result of the teaching provided herein.

Example 1

Preparation of Homeopathic Composition

Mix together the following components 10 ml *Nux Vomica* (5c medicating potency; described above); 100 ml *Taraxacum* (5× medicating potency); 10 ml Calc Carb (5c medicating potency, described above); 10 ml Mag Phos (5c medicating potency as described above).

Add the above contents to 870 ml of 90% ethanol and succuss 20 times. This makes 1000 mls of the medicating potency.

The compositions and methods are further described by the following numbered paragraphs:

1. A homeopathic composition comprising three or more of the following remedies: *nux vomica, taraxacum*, magnesium phosphoricum and calcarea carbonicum.

2. A composition of any of the preceding paragraphs wherein said remedies are in the form of tincture.

3. A composition of any of the preceding paragraphs, wherein said remedies are in the form of ethanolic solutions.

4. A composition of any of the preceding paragraphs, wherein said remedies are in the form of aqueous extracts.

5. A composition of any of the preceding paragraphs further wherein said composition is potentized.

6. A composition of any of the preceding paragraphs, wherein said remedies are potentized.

7. A composition of any of the preceding paragraphs, further comprising a carrier.

8. A composition of any of the preceding paragraphs wherein said carrier is glycerin.

9. A composition of any of the preceding paragraphs, further comprising a preservative.

10. A composition of any of the preceding paragraphs in a form selected from the group consisting of: a solution, an oral tablet, pill, pillule, gel cap, spray and drop.

11. A method to aid weight loss in a mammal comprising administering to said mammal an effective amount of the composition described in any of the preceding paragraphs.

12. The method described in paragraph 11 wherein said mammal is a human.

13. The method described in paragraphs 11 and 12 wherein said administering is accomplished by delivering a solution of a composition described in any of the preceding paragraphs.

14. A homeopathic composition comprising the following remedies: *nux vomica, taraxacum*, magnesium phosphoricum and calcarea carbonicum.

15. A homeopathic composition comprising the following remedies: *nux vomica* or a remedy with a similar profile, *taraxacum* or a remedy with a similar profile, magnesium phosphoricum or a remedy with a similar profile and calcarea carbonicum or a remedy with a similar profile.

16. A homeopathic complex as paragraphed in any of the preceding paragraphs further comprising conventional pharmaceutical excipients and/or carriers.

17. A combination therapy comprising the homeopathic complex as paragraphed in any of the preceding paragraphs and a conventional pharmaceutical.

18. A homeopathic complex as paragraphed in any of the preceding paragraphs for use in therapy 19. A homeopathic complex as paragraphed in any of the preceding paragraphs for use in the treatment of humans and animals.

20. A method for the manufacture of a medicament comprising a homeopathic complex as described in any of the preceding paragraphs for use in weight loss.

Although specific embodiments have been illustrated and described herein, it will be appreciated by those of ordinary skill in the art that any arrangement that is calculated to achieve the same purpose may be substituted for the specific embodiments shown. This application is intended to cover any adaptations or variations that operate according to the principles of the invention as described. Therefore, it is intended that this invention be limited only by the claims and the equivalents thereof. The disclosures of patents, references and publications cited in the application are incorporated by reference herein.

What is claimed is:

1. A homeopathic composition consisting of the following remedies: *nux vomica, taraxacum*, magnesium phosphoricum and calcarea carbonicum.

2. The composition of claim 1 wherein said remedies are in the form of tincture.

3. The composition of claim 1, wherein said remedies are in the form of ethanolic solutions.

4. The composition of claim 1, wherein said remedies are in the form of aqueous extracts.

5. The composition of claim 1 further wherein said composition is potentized.

6. The composition of claim 1, wherein said remedies are potentized.

7. The composition of claim 1, further comprising a carrier.

8. The composition of claim 7 wherein said carrier is glycerin.

9. The composition of claim 1, further comprising a preservative.

10. The composition of claim 1 in a form selected from the group consisting of: a solution, an oral tablet, pill, pillule, gel cap, spray and drop.

11. A method to aid weight loss in a mammal comprising administering to said mammal an effective amount of the composition of claim 1.

12. The method of claim 11 wherein said mammal is a human.

13. The method of claim 11 wherein said administering is accomplished by delivering a solution of the composition of claim 1.

14. A homeopathic composition to aid weight loss in a mammal consisting essentially of the following remedies: *nux vomica, taraxacum*, magnesium phosphoricum and calcarea carbonicum, wherein the *nux vomica, taraxacum*, magnesium phosphoricum and calcarea carbonicum are in a 1:1 ratio with respect to each other.

* * * * *